United States Patent [19]

Phillippi

[11] 4,231,663
[45] Nov. 4, 1980

[54] DEVICE FOR CALIBRATING THE PHOTOMETRIC LINEARITY OF OPTICAL INSTRUMENTS

[76] Inventor: Conrad M. Phillippi, 7420 Brantford Rd., Dayton, Ohio 45414

[21] Appl. No.: 21,142

[22] Filed: Mar. 16, 1979

[51] Int. Cl.³ ........................................... G01N 21/01
[52] U.S. Cl. ................................... 356/432; 250/573; 350/314
[58] Field of Search ................................ 356/432–444, 356/370, 235, 256; 250/343, 573; 350/314

[56] References Cited

U.S. PATENT DOCUMENTS 4,059,357  11/1977  Klein .................................... 356/432

Primary Examiner—John K. Corbin
Assistant Examiner—Bruce Y. Arnold
Attorney, Agent, or Firm—Joseph E. Rusz; Casimer K. Salys

[57] ABSTRACT

A device and method are disclosed for checking photometric linearity of intensity measuring optical instruments which operate by passing a beam of light through samples undergoing analysis. Variable and step attenuators in optical series are introduced into the path of the light beam used by such instruments. The variable attenuator completely obstructs a segment of the light beam and the area of this segment is manually adjustable. The step attenuator, of known accuracy, homogeneously attenuates the full area of the remaining beam. To use the device, the instrument is first adjusted to respond correctly at zero and full scale. The variable attenuator is then inserted into the beam to its selected location and the output response of the instrument is recorded. The output response is again recorded after the step attenuator is inserted into the remaining or unobstructed segment of the light beam. Linearity is checked by comparing output response at diverse settings of the variable attenuator with and without the presence of the step attenuator. The ratios of output response with and without the step attenuator should remain constant irrespective of the variable attenuator setting and will correspond in value to the accurately known effect of the step attenuator in a linear instrument. If sought, an accurate input-output response can be reconstructed by an iterative sequence which begins at the full scale point. From that point the input magnitudes are repetitively reduced by the known effects of the step attenuator, while the output magnitudes are repetitively reduced by smoothed values of the apparent steps obtained during the linearity analysis.

4 Claims, 8 Drawing Figures

DEVICE FOR CALIBRATING THE PHOTOMETRIC LINEARITY OF OPTICAL INSTRUMENTS

RIGHTS OF THE GOVERNMENT

The invention described herein may be manufactured and used by or for the Government of the United States for all governmental purposes without the payment of any royalty.

BRIEF SUMMARY

The present invention is directed to a device and method for checking the photometric linearity of optical instruments, and a method for reconstructing the input-output relationship for calibration purposes when excessive nonlinear performance is detected.

In one form, the device comprises a variable attenuator and a step attenuator inserted in series optically. The variable attenuator is uncalibrated and manually adjustable over the full range of zero to 100 percent attenuation. The step attenuator, on the other hand, is both accurately calibrated and spatially homogeneous as to attenuation irrespective of the size of the light beam passing therethrough. When the step attenuator is inserted into the path of the light beam used by the intensity measuring optical instrument, at diverse settings of the variable attenuator, the output response to the insertion indicates the relative nonlinearity between the input and output of the instrument at the point prescribed by the variable attenuator setting.

The method by which a check is made for nonlinearity and an accurate input-output response curve is reconstructed consists of an iterative sequence commencing with a tabulation of output responses over the full output response range of the instrument. The itensity measuring optical instrument is first adjusted to respond correctly at the opposite ends of the scale, i.e. zero and full scale, with the intermediate nonlinearities being the subject of the inquiry. At each intermediate setting of the variable attenuator the output is recorded both with and without the step attenuator inserted. A calculation is performed to ascertain the apparent step, a ratio between the output response with and without the step attenuator. If the apparent step is substantially identical to the calibrated value of the step attenuator, the instrument is linear. Otherwise, the correct input-output response of the instrument must be reconstructed from the measured data.

The actual input-output response is reconstructed recursively using interpolated or smoothed values of the apparent step from the foregoing measurement sequence and the accurately known value of the step attenuator.

DETAILED DESCRIPTION

Optical instruments which are used to measure light intensity are normally capable of being adjusted to set the zero end output response and the full scale output response. When the instrument is operating properly the intermediate output responses are expected to be linear once the zero and full scale ends are adjusted. For a variety of reasons the instrument may actually be nonlinear, introducing errors into the output data which are not readily detectable.

It is undoubtedly possible to calibrate light intensity measuring instruments, representative of which are the photometer and spectrophotometer. Unfortunately, conventional calibration processes are generally complicated, intensive, demand specialized test equipment or require disassembly of the instrument.

The invention here disclosed provides a comparatively simple device and various methods for not only checking the calibration but also correcting the input-output response curve for nonlinear characteristics detected during the calibration check.

Figure 1:
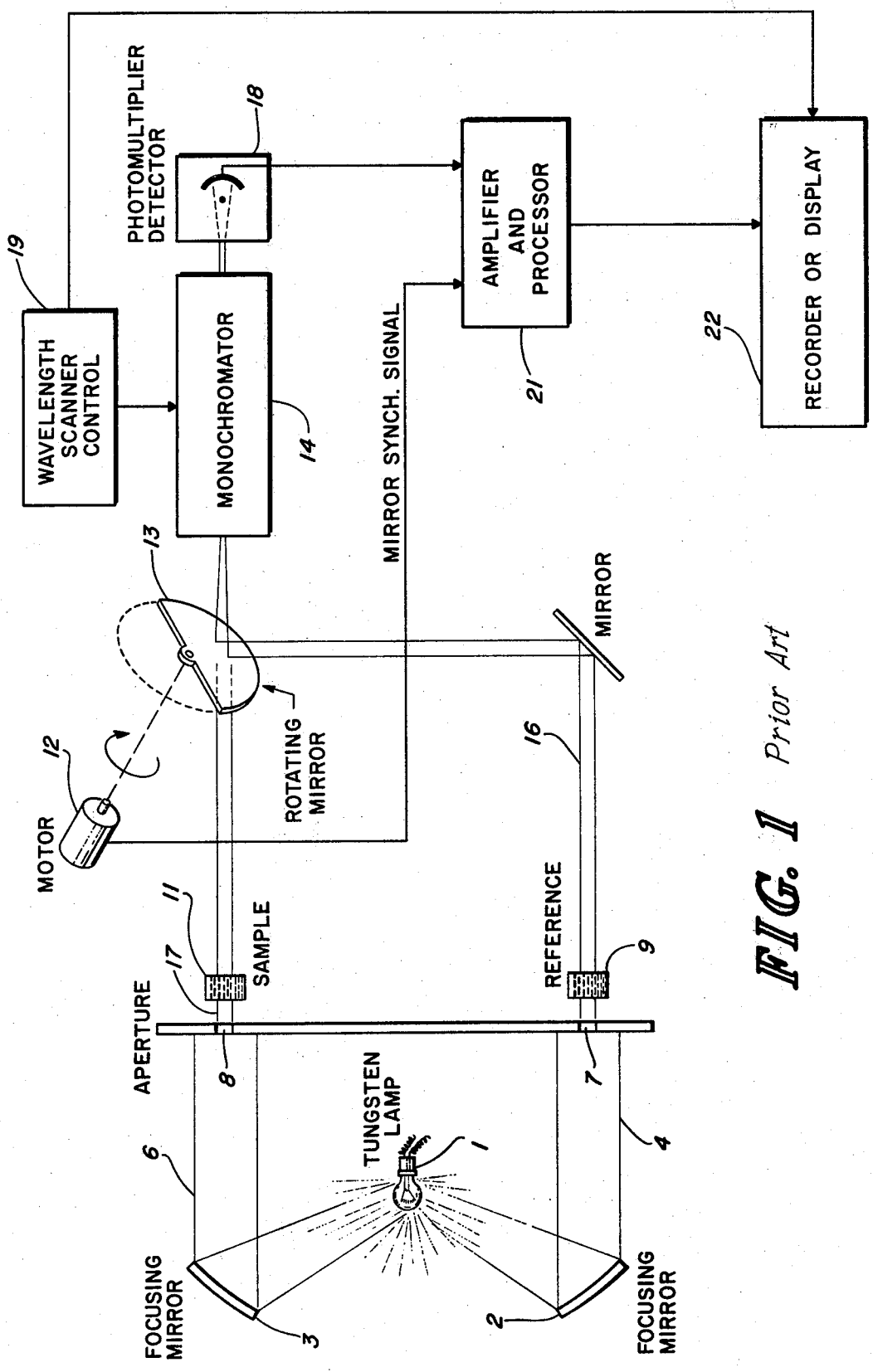
FIG. 1 is a schematic representation of a spectrophotometer type optical instrument.

Turning now to FIG. 1, there appears a schematic of a conventional spectrophotometer. The particular one depicted provides a response based upon the transmittance of material within a cuvette over the full wavelength spectrum being investigated. More particularly, tungsten lamp 1 provides broad spectrum luminous energy which is reflected and focused by substantially identical mirrors 2 and 3. The two focused beams, 4 and 6, are generally homogeneous in luminous energy density, though the invention is not limited by that constraint. Beams 4 and 6 are reduced in size by identical apertures 7 and 8 so that the remaining beam passes through a small segment of reference cuvette 9 and sample cuvette 11, respectively. Reference cuvette 9 is generally used to represent complete transmittance or full scale output of the response. Sample cuvette 11 contains the material whose spectral absorption characteristics are sought.

Motor 12 rotates semicircular shaped mirror segment 13 causing the luminous energy reaching conventional monochromator 14 to alternate between reference beam 16 and sample beam 17. The output of monochromator 14 is detected by photomultiplier 18 while its spectral scan is under the control of wavelength scanner control 19. Amplifier and processor 21 synchronizes the detected signals from multiplier 18 with the position of rotating mirror 13 to coordinate the signal sent to output means 22, typically a strip chart recorder, X-Y recorder or visual display. Reference signals from wavelength scanner control 19 are also sent to output means 22, allowing output responses to be presented in terms of the luminous energy wavelength. Fundamentally, the device depicted in, and described with reference to, FIG. 1 is well known by those practicing in the art.

Figure 2:
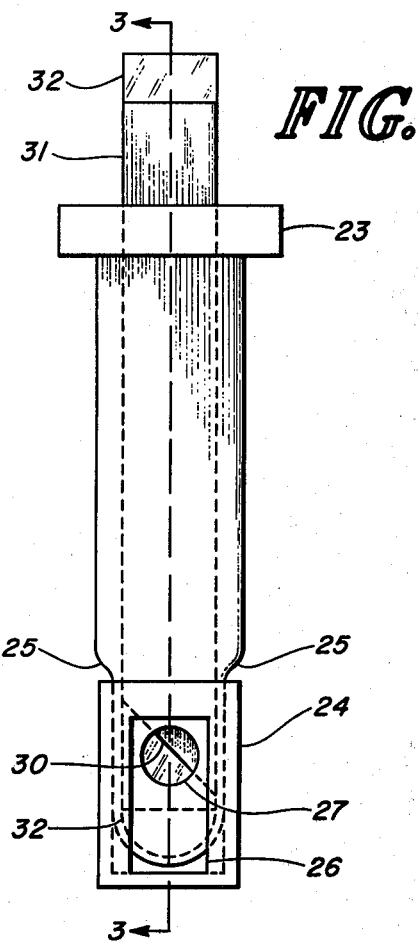
FIG. 2 illustrates one embodiment of the complete attenuation device inserted within a cell holder of a spectrophotometer.
Figure 3:
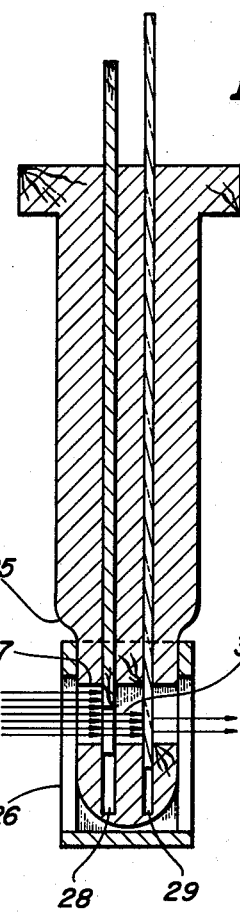
FIG. 3 is a cross-sectional schematic of the embodiment in FIG. 2, taken at section line 3—3.

One embodiment of the calibration checking device appears in FIG. 2, where body 23 is tapered at shoulders 25 for fixed insertion into conventional cuvette holder 24. FIG. 3 is a cross-sectional schematic of the complete device taken at section lines 3—3 of FIG. 2. Body 23 of the embodiment is cylindrical above shoulder 25, and of square cross section below shoulder 25 to permit insertion and fixed orientation in cuvette holder 24. Rectangular openings 26 on both sides of cuvette holder 24 allow unobstructed passage of light beams directly through the cuvette, replaced here by the lower end of the calibration checking device. Vertically disposed in body 23 of the device are two rectangular channels 28 and 29 within which are slidably located two attenuator elements, variable attenuator element 31 and step attenuator element 32. Both attenuator elements are capable of being slid vertically in their respective channels and positioned transverse to passage 27 so as to obstruct portions thereof. For purposes of this embodiment the bottom edge of variable attenuator element 31 has a diagonal edge, 30.

The embodying structure appearing in FIGS. 2 and 3 was reduced to practice with readily available construction materials, wood for body 23 and variable attenuator element 31. Step attenuator 32 was fabricated from conventional slide glass material.

To undertake a calibration check the device is inserted into the cuvette holder, as shown in FIG. 2, and substituted in place of sample 11. Once aligned, sample beam 17 freely passes through passage 27 when attenuator elements 31 and 32 are withdrawn from the passage. Variable attenuator 31 is then inserted to a depth sufficient to obstruct part of sample beam 17, as exemplified by its location in FIGS. 2 and 3. Since the variable attenuator does not contribute directly to the calibration accuracy, no significant precision is actually associated with locating the variable attenuator. Step attenuator 32 has only two positions in the calibration process. A first position where it is completely withdrawn from passage 27, and a second, fully inserted position, where it completely covers passage 27.

The essential operating principle of the device is one of perturbation with a step attenuator of high accuracy at points of various output magnitude to compare the known input change with the indicated output response. Consider, for purposes of elaboration, that the step attenuator is designed to attenuate 10%, i.e. transmit 90%. If the variable attenuator is randomly set to produce an output response at 71% of full scale (FS) with the step attenuator absent, the output should drop to 63.9% (71-7.1) when the 10% step attenuator element is inserted into the device. Any output different from 63.9% indicates a nonlinearity in the region of the 71% output response. Alternately, the apparent step, 63.9/71=0.9, can be calculated from the test data and compared to the precisely known transmittance of the step attenuator. Note that the actual relationship between the input, as set by the variable attenuator, and the output response, showing 71%, is not sought directly.

Figure 4:
FIGS. 4, 5 and 6 are various embodiments of the step attenuator.
Figure 5:
Figure 6:

Body 23 of the device is made from an opaque material. Likewise, variable attenuator element 31 is fabricated from a material which is opaque at all wavelengths over which the spectrophotometer in FIG. 1 will operate. Step attenuator 32 is partially transmissive, the particular embodiment described hereinafter being in the range of 90%, and as a general rule is constant in magnitude and of known accuracy for all the sample beam wavelengths being evaluated. In FIG. 4 step attenuator element 32 is shown as slide glass, but could, as depicted in FIGS. 5 and 6, be made in the form of a grid, 33, or a mesh, 34. In addition to correcting for the effects of reflection and diffraction, the grid and mesh type attenuators would of necessity have to attenuate homogeneously over the whole of any area exposed to sample beam 17. This point is apparent when one reflects on the sample beam appearing schematically in FIG. 3, since by definition attenuated sample beam 36 must be an accurate and unvarying fraction of beam 37, irrespective of where variable attenuator element 31 is positioned.

The method by which the device described hereinbefore is utilized to check the calibration of a spectrophotometer of the type depicted in FIG. 1 is preferably exemplified by analyzing the test results and calculations attributable to an actual test of one embodiment. In this particular case, inquiry was directed to a single wavelength of 5500 angstroms with step attenuator element 32 fabricated from slide glass having a transmittance of 91.6%.

TABLE I

| $O_i$ Indicated output signal with just the variable attenuator inserted (% of full scale) | $O_f$ Indicated output signal with both attenuators inserted (% of full scale) | $S_a = \dfrac{O_f}{O_i}$ Apparent Step (%) |
| --- | --- | --- |
| 100 | 91.4 | 91.4 |
| 95 | 86.6 | 91.2 |
| 89 | 81.2 | 91.2 |
| 84 | 76.4 | 90.9 |
| 78 | 70.9 | 90.9 |
| 73 | 66.3 | 90.8 |
| 67 | 60.9 | 90.9 |
| 62 | 56.4 | 91.0 |
| 57 | 51.8 | 90.8 |
| 51 | 46.3 | 90.7 |
| 45 | 41.0 | 91.0 |
| 40 | 36.3 | 90.7 |
| 34 | 30.8 | 90.7 |
| 29 | 26.2 | 90.4 |
| 22 | 19.9 | 90.5 |
| 18 | 16.2 | 90.2 |
| 12 | 10.8 | 89.6 |
| 9 | 8.0 | 89.0 |

Table I contains the raw measurement data. As in normal use the spectrophotometer is initially preset so that the inputs and outputs correspond at zero and full scale. $O_i$ is the initial output set by means of variable attenuator element 31 in a generally descending sequence. $O_f$ is the final output, after effects of step attenuator 32 have been introduced. The apparent step, $S_a$, is defined hereinbefore as the ratio of $O_f/O_i$. For the slide glass attenuator which transmits 91.6%, any departure in $S_a$ from that amount indicates local nonlinearity in the input-output relationship, notwithstanding the fact that the zero and full scale points remain unaltered from the original adjustment. The $S_a$ data from Table I is plotted on the graph in FIG. 7.

It is readily apparent to one skilled in the art that $S_a$ values in range 38, at the lower end of the output scale, are more susceptible to error since the output change attributable to inserting the step attenuator is a fraction of an already low output value. Recording or display errors become significant unless appropriate linear amplification is added when operating in this region.

Figure 7:
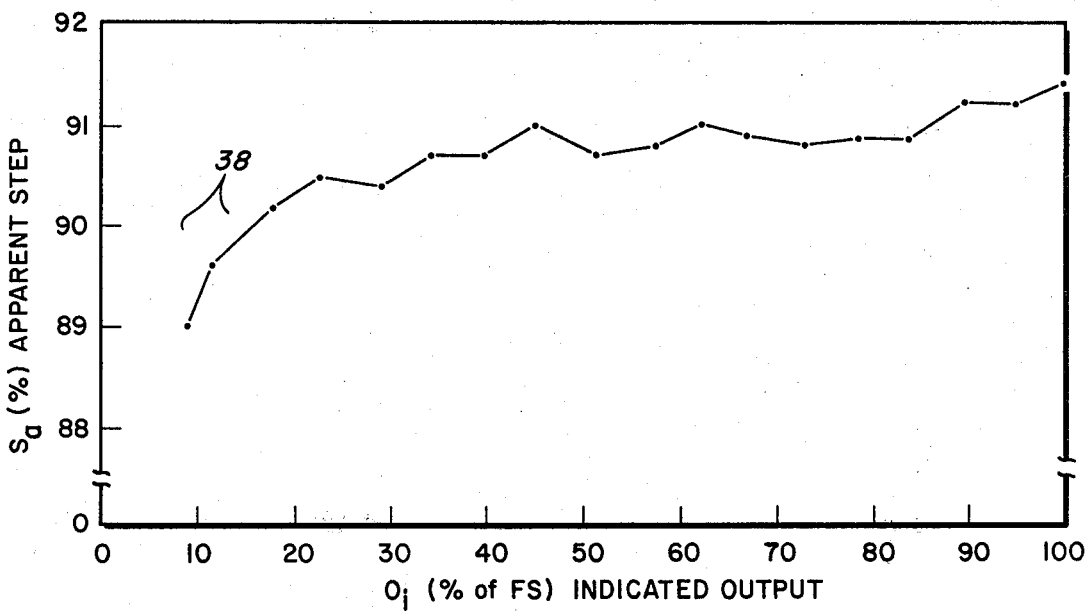
FIG. 7 is a plot of apparent step verses indicated output.

Having detected the existence of a nonlinearity, a further refinement of the method uses the apparent step ($S_a$) data plotted in FIG. 7, interpolating between points when necessary, to reconstruct the actual input-output relationship between the intensity of beam 17 after it is attenuated by sample 11 and the output response appearing in output means 22. Obviously, as the number of $O_i$ and $O_f$ data samples increase greater refinement is injected into the interpolation process, and improved accuracy results in the reconstructed input-output relationship.

TABLE II

| $O_i$ (% of full scale) | Interpolated $S_a$ $S_a'$ (%) | $O_f' = O_i \times S_a'$ (% of full scale) | $I_i$ (% of full scale) | $I_f$ (% of full scale) |
|---|---|---|---|---|
| 100% | 91.4 | 91.4% | 100% | 91.6% |
| 91.4 | 91.2 | 83.36 | 91.6 | 83.91 |
| 83.36 | 90.85 | 75.73 | 83.91 | 76.86 |
| 75.73 | 90.82 | 68.78 | 76.86 | 70.40 |
| 68.78 | 90.85 | 62.49 | 70.40 | 64.49 |
| 62.49 | 90.97 | 56.84 | 64.49 | 59.07 |
| 56.84 | 90.78 | 51.60 | 59.07 | 54.11 |
| 51.60 | 90.70 | 46.80 | 54.11 | 49.56 |
| 46.80 | 90.92 | 47.55 | 49.56 | 45.40 |
| 42.55 | 90.85 | 38.66 | 45.40 | 41.59 |
| 38.66 | 90.70 | 35.07 | 41.59 | 38.09 |
| 35.07 | 90.70 | 31.80 | 38.09 | 34.89 |
| 31.80 | 90.58 | 78.81 | 34.89 | 31.96 |
| 28.81 | 90.40 | 26.04 | 31.96 | 29.28 |
| 26.04 | 90.44 | 23.55 | 29.28 | 26.82 |
| 23.55 | 90.48 | 21.31 | 26.82 | 24.57 |
| 21.31 | 90.42 | 19.27 | 24.57 | 22.50 |
| 19.27 | 90.31 | 17.40 | 22.50 | 20.61 |
| 17.40 | 90.22 | 15.70 | 20.61 | 18.88 |
| 15.70 | 90.00 | 14.13 | 18.88 | 17.29 |
| 14.13 | 89.83 | 12.69 | 17.29 | 15.84 |
| 12.69 | 89.68 | 11.38 | 15.84 | 14.51 |
| 11.38 | 89.60 | 10.20 | 14.51 | 13.29 |
| 10.20 | 89.32 | 9.11 | 13.29 | 12.18 |
| 9.11 | 89.12 | 8.12 | 12.18 | 11.15 |
| 8.12 | 89.00 | 7.22 | 11.5 | 10.22 |
| 7.22 | | | 10.22 | |

Reconstruction of the input-output relationship involves an interactive sequence best described with reference to Table II. $I_i$ and $I_f$ represent the initial and final values of light intensity input, with the variable attenuator alone and with both attenuators inserted, respectively. Since the effect of the step attenuator is known, $I_f$ is always 91.6% of $I_i$. $S_a'$, interpolated $S_a$, is for present purposes a straight line average between data points in FIG. 7, though it could also be smoothed by any one of many mathematic or graphic techniques. $O_f'$ is equal to the multiple of $O_i$ and the $S_a'$, with the value for $S_a'$ taken directly from FIG. 7 at the appropriate $O_i$ value.

Beginning with $I_i$ and $O_i$ at 100%, the adjusted full scale relationship, the first $O_f'$ value is determined by taking $S_a'$ (91.4%) from FIG. 7 and multiplying it with the $O_i$ value; the result being $O_f'$ at 91.4% as appears in the table. Since the input $I_f$ is always 91.6% of $I_i$, the corresponding input for output $O_f'$ at 91.4% is $I_f$ at 91.6%. These values for $O_f'$ and $I_f$ then serve as the respective starting points for the ensuing calculation of $O_f'$ and $I_f$. For example in the second row of the table, $O_i$ is now 91.4% ($O_f'$ from the previous row), $S_a'$ is read from FIG. 7 as 91.2%. $O_f'$ is then calculated to be 83.36%. The input tabulation is independent of the output tabulation with the second row now showing $I_i$ at 91.6% (the previous $I_f$) and $I_f$ calculated to be 83.91% (91.6%×91.6%). The process is repeated for the subsequent rows.

Figure 8:
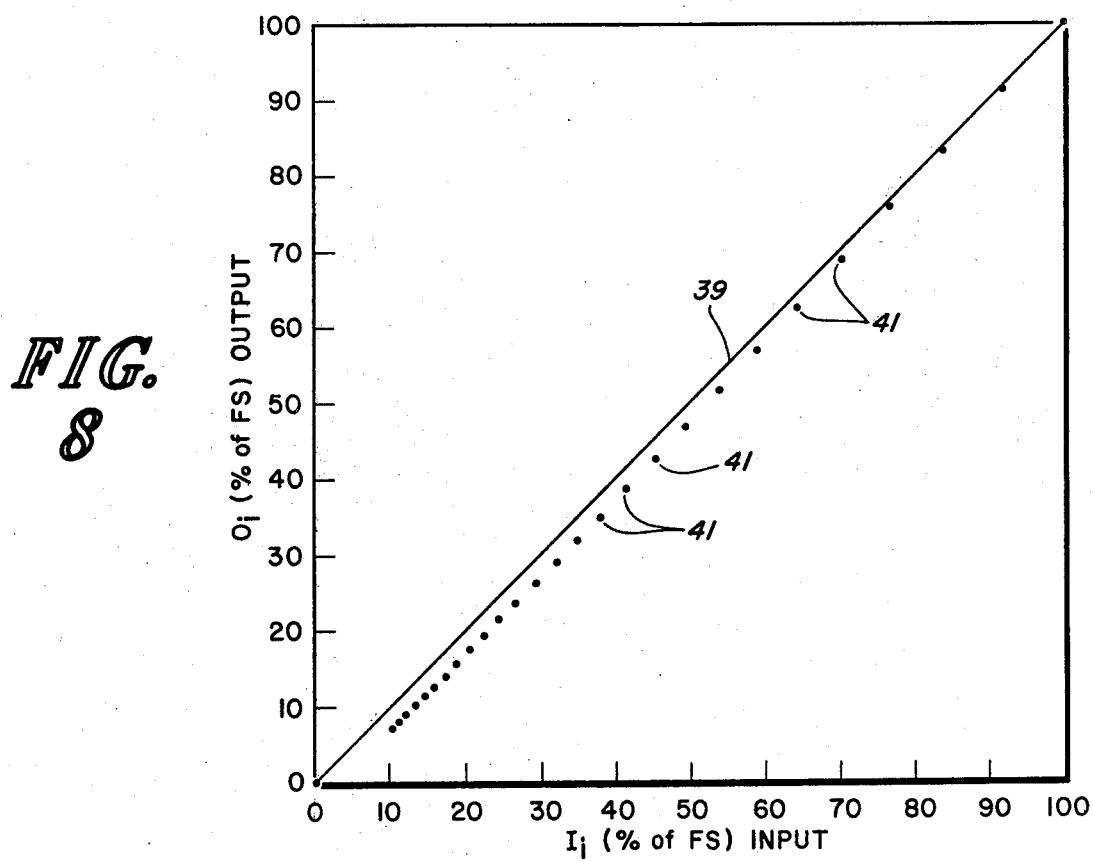
FIG. 8 contains a reconstructed input-output plot of the spectrophotometer undergoing calibration.

The reconstructed input-output relationship for the embodiment shown and tabulated appears in FIG. 8. The input values $I_i$ are taken along the abscissa while the corresponding outputs $O_i$ are along the ordinate. The actual values are obtained from Table II beginning at 100%, then proceeding row by row, matching the corresponding values of input $I_i$ and output $O_i$. The point at the origin of the plot is based on the zero point adjustment of the spectrophotometer prior to undergoing calibration checking. Straight line 39 represents the ideal input-output line, while points 41 describe the actual path of the relationship.

The actual input-output relationship described by data points 41 in FIG. 8 provides a direct means by which the user of the spectrophotometer can readily ascertain the actual magnitude of the light energy passing through sample 11. The actual amounts are those values of $I_i$ which correspond to displayed outputs $O_i$ as defined by the relationship curve joining data points 41.

The input-output test was performed on a spectrophotometer at a wavelength of 5500 angstroms. One skilled in the art will recognize that comparable analysis must be performed at other wavelengths and scale settings over the full operating range of the instrument to completely verify its correct operation.

It is equally apparent that the process disclosed herein is highly repetitive, and therefore, readily amenable to computer processing. Furthermore, the burdensome reconstruction portion of the process is likely to be used less frequently than the calibration check sequence in which apparent step $S_a$ alone is determined. If $S_a$ indicates acceptable accuracy, reconstruction of the actual input-output relationship is of marginal benefit to the instrument user.

I claim:

1. A device for calibrating the photometric linearity of optical instruments which transmit a light beam through the sample being analyzed, which comprises a variable attenuator which can be inserted into the path of said light beam, and when so inserted completely obstructs an area segment of said beam without altering the remainder of the beam area, and an accurate step attenuator of fixed value, capable of being inserted into and removed from the path of the beam segment not obstructed by said variable attenuator.

2. The device recited in claim 1, wherein said step attenuator provides a homogeneous level of optical attenuation across the path of the light beam passing therethrough.

3. A method for checking the photometric linearity of optical instruments which transmit a light beam through the sample being analyzed, comprising the steps of:
   a. adjusting the input and output of the optical instrument at the zero and full scale ends;
   b. inserting a variable attenuator into the light beam so that a segment of the beam is completely obstructed, and recording the corresponding output response;
   c. without moving the variable attenuator, inserting an accurate step attenuator into the path of the remaining beam, and recording the output response;
   d. calculating the apparent step at each setting of the variable attenuator by taking the ratio of the readings with and without the step attenuator inserted; and
   e. repeating steps b, c, and d with different settings of the variable attenuator.

4. The method as recited in claim 3, including the further steps of:
   a. calculating a sufficient number of apparent step values over the output range of the instrument to establish a mathematical relationship between the apparent step and the output magnitude.
   b. iteratively calculating and tabulating the input and output of the instrument beginning with zero attenuation input and full scale output, where the input is repetitively reduced by the known value of the step attenuator, and where the output is repetitively reduced by using a smoothed value of the apparent step corresponding to that output magnitude; and
   c. reconstructing the input-output response of the instrument by plotting the corresponding input and output steps tabulated in step b.

* * * * *

UNITED STATES PATENT AND TRADEMARK OFFICE
CERTIFICATE OF CORRECTION

PATENT NO. : 4,231,663

DATED : November 4, 1980

INVENTOR(S) : Conrad M. Phillippi

It is certified that error appears in the above—identified patent and that said Letters Patent are hereby corrected as shown below:

Col 2, line 50, change "multiplier" to --- photomultiplier ---.

Col 5, line 25, TABLE II, fourth column($I_i$) of figures from left, change "11.5" to --- 11.15 ---.

Signed and Sealed this

Twenty-fourth Day of March 1981

[SEAL]

Attest:

RENE D. TEGTMEYER

Attesting Officer    Acting Commissioner of Patents and Trademarks